United States Patent [19]

Boricheski, deceased

[11] 3,972,323

[45] Aug. 3, 1976

[54] ORTHOPEDIC BANDAGE

[75] Inventor: Joseph H. Boricheski, deceased, late of South River, N.J., by Helen Grabiek, executrix

[73] Assignee: Johnson & Johnson, New Brunswick, N.J.

[22] Filed: Jan. 31, 1975

[21] Appl. No.: 546,160

[52] U.S. Cl. ............................................. 128/91 R
[51] Int. Cl.² ........................................... A61F 5/04
[58] Field of Search ............... 128/90, 91 R, 89, 87

[56] References Cited
UNITED STATES PATENTS

| | | | |
|---|---|---|---|
| 2,127,552 | 8/1938 | Danmen | 128/90 |
| 2,375,365 | 5/1945 | Howald et al | 128/90 X |
| 2,616,418 | 11/1952 | Eberl | 128/90 |
| 2,625,733 | 1/1953 | Secrist | 128/91 R |
| 2,842,121 | 7/1958 | Billings et al. | 128/91 R |
| 2,935,065 | 5/1960 | Homier et al. | 128/91 R |
| 3,089,486 | 5/1963 | Pike | 128/90 |
| 3,485,706 | 12/1967 | Evans | 19/161 |
| 3,618,599 | 11/1971 | Beightol | 128/90 |

*Primary Examiner*—John D. Yasko
*Attorney, Agent, or Firm*—Steven P. Berman

[57] ABSTRACT

A highly conformable orthopedic bandage which exhibits a high "green strength" is provided for immobilizing or supporting parts of the body comprising a textile-like, apertured, porous, nonwoven polyester fabric of essentially unbonded, mechanically entangled fibers randomly entangled with each other in a pattern of localized entangled regions interconnected by fibers extending between adjacent entangled regions, impregnated with a settable composition.

3 Claims, No Drawings

ORTHOPEDIC BANDAGE

BACKGROUND OF THE INVENTION

The present invention relates to orthopedic bandages which are used to form casts for immobilizing and supporting parts of the body to permit undisturbed healing. More specifically, the invention relates to plaster of Paris containing compositions and carrier materials therefor, which upon activation by wetting, are very soft and conformable, permitting the formation of a smooth, aesthetically pleasing cast; and which exhibit a high green strength permitting early ambulation.

Orthopedic bandages have heretofore been made by coating a flexible carrier or backing with a settable composition. The carrier or backing material generally has been of woven gauze. The settable composition has been of the kind which can be activated by some solvents, heat or irradiation. The bandage is usually in a strip form, wound into a roll or precut to the desired shape. Some bandages are activated just prior to application while others can be cured in place on the body member.

It is important that an orthopedic bandage be soft and conformable to the body member so that a smooth, comfortable cast is formed without ridges or wrinkles which on curing does not create pressure points next to the skin. It is also important that the cast forming material cures rapidly enough and reaches sufficient strength to permit early ambulation.

It has been observed that a low count woven fabric, employed as a carrier for settable compositions, is quite satisfactory for general purpose orthopedic bandages. However, its lack of conformity is a considerable disadvantage when wrapped over uneven surfaces. Also, on application the edge threads tend to become detached from the bandage due to raveling, which interferes with obtaining a smooth and uniform wrap. This lack of conformity can be overcome by the use of elastic warp stretch yarn constructions, some of which are fully conformable. However, they are expensive to manufacture and their elastic properties are difficult to control. Furthermore, some edge threads still ravel and short threads come loose during bandage application.

Other backing materials, such as foam, paper and nonwoven fabrics have also been tried without much success primarily because of their insufficient strength either during the manufacturing process or on application. Efforts to improve strength by increasing their thickness resulted in high bulk and poor lamination of the cast.

Another disadvantage of some cast-forming materials is their insufficient early cast strength which necessitates patients to remain relatively motionless for a substantial length of time. Cast strength and especially early cast strength depend on both the backing material and the settable composition employed and also on the nature of the coating or impregnation of the backing by the settable composition.

Attempts to provide for high early cast strength in an orthopedic bandage, hereafter referred to as "green strength" (as measured one hour after cast application), together with good conformability have proved largely unsuccessful.

It is, therefore, a principle object of the invention to provide a cast-forming material that possesses high green strength thereby permitting early ambulation of the patient. It is a general object of the present invention to provide an orthopedic bandage which is highly conformable and which can be applied over uneven surfaces of the body without the danger of creating pressure points on the skin. Concomitantly, it is also an object to provide an orthopedic bandage that does not suffer the disadvantage of raveling during the wrapping procedure. A still further object is to prepare a cast-forming material with a carrier or backing strong enough to withstand stresses to which it may be subjected during the coating process.

SUMMARY OF THE INVENTION

It has been surprisingly found that these objects may be achieved by an orthopedic bandage comprising a substrate or carrier of a textile-like, apertured, porous, nonwoven polyester fabric of unbonded, mechanically entangled fibers randomly entangled with each other in a pattern of localized entangled regions interconnected by fibers extending between entangled regions impregnated with a settable composition. Other nonwoven fabrics of similar character, made of other than polyester fibers, such as, for example, rayon, were found unsuitable as a carrier for the settable composition in the orthopedic bandages of the present invention. Nonwoven fabrics made of blends of fibers, such as for example, a polyester-rayon blend, or nonwoven fabrics made by the use of binders were also found unsatisfactory as a substrate or carrier for the settable composition in the orthopedic bandages according to the present invention.

As indicated earlier, the nonwoven polyester fabric is prepared by mechanical entanglement without the use of binders. Besides this basic requirement of mechanical entanglement, the nonwoven polyester fabric must meet additional requirements in order that it be suitable for use in the orthopedic bandages of the present invention.

In order to maintain its structural integrity under the conditions of process and use, the nonwoven fabric should have a tensile strength of at least about 1 pound per inch width of the fabric and, preferably, at least about 3 pounds. Although fabrics having a tensile strength of about 20 to about 25 pounds per inch width of the fabric can be utilized, they are not ordinarily made based on economic considerations.

For the purpose of providing good conformability in the orthopedic bandage, the carrier on substrate should have an extent of elongation of about 25 to 100% in machine direction and of about 40 to 120% in cross direction, and preferably an extent of elongation of about 35 to 90% in machine direction and of about 40 to 110% in cross direction, of its relaxed length and width respectively.

To provide open areas within the matrix of the carrier for containing sufficient amounts of a settable composition, the nonwoven fabric should have about 50 to 500 apertures per square inch with an aperture size of about 1/64 × 1/64 to ⅛ × ⅛ inches and preferably about 80 to 200 apertures per square inch with an aperture size of about 3/64 × 3/64 to 7/64 × 7/64 inches.

A fabric weight of about 0.5 to 3.0 ounces per square yard and preferably of about 0.75 to 2.0 ounces per square yard was found to be desirable for the purposes of the present invention. The weight of the fabric influences, besides bulk, strength and drapability.

The mechanically entangled nonwoven polyester fabric having the above-described characteristics is impregnated with a settable composition. The preferred settable composition is a water-activable plaster of Paris composition alone or a plaster of Paris composition with modifying agents, such, for example, as described in U.S. Pat. Nos. 2,557,083, 2,842,138 and 3,746,680. However, settable compositions of the kind which can be activated by solvents, heat or irradiation prior to application or in place may also be used to advantage in the present invention.

In the preferred practice of the present invention, the plaster of Paris is applied from an aqueous slurry to the carrier fabric by coating one side of the fabric using conventional metering rolls or knives.

While from the standpoint of simplicity of operation and required apparatus it is preferred to impregnate the fabric by coating one side of the fabric, it is to be understood that, the impregnation may also be accomplished by coating the fabric on both sides thereof.

The impregnated fabric is then dried and cut to desired shapes and forms or rolled up and packaged. A cast is prepared by taking a piece or a roll of this material, immersing the same in water for a few seconds, removing, squeezing out the excess water, and applying in the conventional manner of applying plaster of Paris bandage wraps.

DETAILED DESCRIPTION OF THE INVENTION

The carrier or substrate which supports the settable composition is a nonwoven polyester fabric which can be made in accordance with the teachings of U.S. Pat. No. 3,485,706 issued to F. J. Evans on Dec. 23, 1967. This fabric comprises polyester fibers locked into place by fiber interaction to provide a strong cohesive structure which maintains its structural integrity without the need for adhesive binders or filament fusing. The fabric has a pattern of entangled fiber regions of higher area density than the average area density of the fabric as a whole and there are interconnecting fibers which extend between the dense entangled regions and are randomly entangled with each other in the dense entangled regions. The entanglement is accomplished by first preparing a loose layer of polyester fibers and then treating the layer with liquid, jetted at a pressure of at least 200 p.s.i. from a row of small orifices, to convert the layer directly into the nonwoven fabric.

It has been discovered that by incorporating certain of the mechanically entangled fabric made by this process into orthopedic bandage, many of the drawbacks heretofore associated with prior orthopedic bandages are obviated.

The fibers should be of a staple length and denier with which sufficient strength can be obtained. Fibers with a denier within the range of from about 0.5 to about 6.0 are usable with a range of about 1.0 to about 3.0 being preferable. Fiber staple lengths of from about 0.25 to about 2.0 inches are suitable with lengths of about 0.5 to about 1.5 inches being preferable. The fabric weight per unit area may vary from about 0.5 to about 3.0 ounces per square yard depending upon the degree of bulk and drapability desired in the final product. Preferably, the weight per unit area should be about 0.75 to about 2.0 ounces per square yard.

In order to achieve the objectives of the present invention, the fabric should have a degree of mechanical entanglement sufficient to permit the resulting product to maintain its structure of integrity under both the conditions of process and use. Specifically, it has been found that the fabric should have a tensile strength of at least about 1 pound, and preferably at least about 3 pounds, per inch width of the fabric. The tensile strength is defined as the force, expressed in pounds per inch-width of the fabric, required to break the fabric. It is determined, by clamping at both ends using a suitable instrument, a 1 inch wide and 6 inch long strip of a sample and exerting a steady 12 inch per minute pull on the fabric. The force required to break the fabric is recorded as the tensile strength of the fabric.

It is important in the instant invention that the above-defined minimum tensile strength be accomplished essentially by a sufficient degree of mechanical entanglement rather than by the use of adhesive binders. When a bonded nonwoven polyester is used as the substrate for the settable composition, a low green strength results upon formation of the cast. Still another drawback resulting from the use of binders is the reduction in conformability of the fabric caused by the relative rigidity of the bonded areas.

In order to obtain good conformability, it is important that the nonwoven fabric possess an elongation of from 25 to 100% in machine direction and of from 40 to 120% in cross direction, and preferably of from 35 to 90% in machine direction and of from 40 to 110% in cross direction. This degree of elongation allows the practitioner to wrap the uneven surface of a body member without creases or wrinkles in the bandage which can cause pressure points on the skin after cast formation. Elongation, expressed as a percentage, is the ratio of the length of extension at the point of break of the fabric to the original length of the fabric.

Although it is possible to prepare orthopedic bandages utilizing carrier materials where the elongation properties fall outside the above-set range, it has been found that the objectives of the present invention cannot fully be met with such due to their lack of sufficient conformability. While on the one hand, a bandage having a lesser degree of elongation than that specified above will not extend sufficiently to conform to irregular shapes of the body member being wrapped, a bandage having elongation properties which exceeds the above-set range will suffer from excessive stretching and concomitant "neck-in" or shrinkage in cross direction of the fabric.

It is also necessary that the fabric utilized in the present invention be apertured. The apertures serve as miniature containers for the settable material and insure its containment during the initiating and wrapping procedures. The fabric with apertures closely resembles the familiar gauze used as a substrate or carrier in orthopedic bandages. The apertures may be formed in the fabric by methods well known in the art, such as, for example, by a jet of fluid impinging on the fabric which is supported on a patterned substrate. A degree of openness of about 50 to 500 holes per square inch were found to be necessary along with hole-sizes in the ranges of $1/64 \times 1/64$ to $1/8 \times 1/8$ inches. In the preferred embodiment, apertures of from $3/64 \times 3/64$ to $7/64 \times 7/64$ inches are used with a degree of openness of from 80 to 200 apertures per square inch. The selection of the degree of openness of the nonwoven polyester fabric is mainly dependent on the type of impregnating or coating process. Namely, when a conventional one side coating process is employed, a higher degree of openness is desired so that sufficient penetration of the settable material through the apertures is achieved. Such penetration will provide for direct contact between the settable material of one layer and the settable material of the next layer when the bandage is wrapped on the patient, thereby contributing to a higher green strength. When a two side coating is used for the impregnation of the nonwoven polyester fabric, the degree of openness may be much less, since penetration of the material through the apertures is easily achieved due to complete immersion of the fabric into the slurry composition of the settable material.

THE SETTABLE COMPOSITION AND IMPREGNATION OF THE FABRIC

The preferred settable composition for use in the present invention is plaster of Paris, however, the invention is not limited to the use of plaster of Paris but may be practiced with other cast forming materials which can be coated onto the nonwoven polyester fabric in a pasty or fluid state, dried, and then activated with suitable activating means so as to again assume a pasty or fluid condition before setting into its final hard state. Such settable materials include those that can be activated by the use of solvents, heat or irradiation.

The plaster of Paris used for the purposes of the present invention may be ordinary plaster of Paris, the type conventionally incorporated in plaster of Paris bandages or the high strength type plaster of Paris commonly known as "alpha gypsum," described in U.S. Pat. No. 1,901,051.

Prior to its application to the carrier, the plaster of Paris is made into a paste or slurry employing a suitable dispensing liquid. About 30 to about 85 parts by weight of liquid per 100 parts by weight of the plaster of Paris are utilized with the preferred embodiment being about 30 to about 60 parts of water per 100 parts by weight of plaster of Paris.

Additives, such as adhesives and retarders, may be introduced into the slurry. Both wet and dry adhesives may be added to prevent the loss of the plaster of Paris composition, either while the cast-forming material is still in the dry state or after it has been immersed in water. Suitable adhesives are, for example, water-insoluble polymers and copolymers of vinyl acetate and methyacrylate or acrylate esters, water-soluble cellulosic ethers and esters, natural resins and those derivatives of resins which are water-insoluble, and solubilized dextrin or starch.

When water is employed as the dispersing liquid, measures must be taken to prevent premature hydration of the plaster of Paris. This can be accomplished by adding a plaster of Paris hydration retarder. Examples of such retarders are ammonium borate and acetic acid. A preferred hydration retarder is a mixture of boric acid and ammonium hydroxide which forms a borate complex which can be decomposed and volatilized during the later drying process.

If volatile additives are added, it is desirable to control temperature to avoid significant loss of such additives by volatilization. For example, when ammonium hydroxide is used, the slurrying step should be carried out at temperatures around 40°C. to prevent premature volatilization of the additive.

Table I below lists the components of a typical plaster of Paris slurry which can be employed in the present invention.

TABLE I

| Component | Composition, Parts by wt. | Function |
|---|---|---|
| Boric acid | 0.4 | Hydration retarder |
| Ammonium hydroxide (28% ammonium) | 0.8 | Hydration retarder |
| Emulsion containing polyvinyl acetate (55% polyvinyl acetate) | 1.5 | Wet adhesive |
| Corn dextrin | 1.5 | Dry stiffening agent, dry adhesive |
| Potassium sulfate | 0.3 | Setting accelerator |
| Alkanol B* | 0.05 | Wetting Agent |
| Water | 50.0 | Dispersing liquid |
| Alpha calcium sulfate hemihydrate | 100.0 | Settable inorganic |

*Trademark of E. I. DuPont de Nemours & Co., Inc. for a sodium naphthyl sulfonate.

This plaster of Paris slurry may be applied to the nonwoven polyester fabric by the conventional technique of coating one side of the fabric, or the technique of coating both sides of the fabric may also be utilized depending on the degree of openness of the fabric and the consistency of the slurry. Such techniques involve the spreading of the slurry on the carrier material after which the carrier and the applied slurry are dried, preferably in either electric or gas-heated circulating air ovens, at temperatures ranging from 100° to 300°C. Preferably, the drying occurs at 150° to 250°C., a specific drying temperature being dependent upon such factors as the dryer dwell time, the particular type of drying equipment used, and the volumetric flow rate in the case of circulating air ovens.

The resulting orthopedic bandages of the present invention have an aesthetically pleasing appearance; no raveling occurs during its wrapping and smoothing operation; and exhibit high green strength.

Green strength is measured one hour after the cast formation.

THE GREEN STRENGTH TEST

A 3 inch by 1 yard bandage strip is rolled into a cylinder form and dipped into water. The wet cylinder form is then wrapped completely upon itself on a one inch diameter steel tubular core, thus, open removal of the steel tubular core in 20 minutes, forming a three inch long, hollow cylinder with a one inch inside diameter. After a period of one hour at room temperature, the cylinder is subjected to a measured force sufficient to deform it by 25%, the force being applied against the cylindrical configuration of the cast shell at a crushing speed of one inch per minute, with a Dillon Dynamometer.

To illustrate the significant green strength advantages of the orthopedic bandages of the present invention over gauze bandages, Examples 1 through 7 are provided. It is to be noted, however, when comparing the green strength of different samples, that these values are very much dependent on experimental conditions. such as, for example, the way the bandage strip is rolled into a cylinder form, and dipped into water. It is, therefore, important to compare the green strength values to the green strength of a gauze sample as the reference standard run at the same time under identical experimental conditons. Examples 8a through d serve as reference guaze samples. Furthermore, for being more informative, % green strength of a sample over green strength of the reference gauze standard is also given for the Examples 1 through 7. Examples 9 and 10 illustrate that an orthopedic bandage having a substrate with a binder and/or having a substrate other than a polyester fabric are inferior in green strength to gauze orthopedic bandages. These samples were run under approximately identical experimental conditions.

EXAMPLE 1

The slurry composition of Table I is coated on one side of a nonwoven 100% polyester fabric of one ounce weight per square yard having 570 apertures per square inch therein with an average aperture size of 1/64 × 4/64 inches. After drying, a 3 inch by 1 yard bandage strip weighing 41 grams is subjected to the Green Strength Test procedure previously described. The results of the test are reported in Table II.

EXAMPLE 2

The slurry composition of Table I is coated on one side of a nonwoven 100% polyester fabric of 0.9 ounce weight per square yard having 190 apertures per square inch therein with an average aperture size of 4/64 × 4/64 inches. After drying, a 3 inch by 1 yard bandage strip weighing 40 grams is subjected to the Green Strength Test procedure. The results of the test are reported in Table II.

EXAMPLE 3

The slurry composition of Table I is coated on one side of a nonwoven 100% polyester fabric of 1.1. ounce weight per square yard having 98 apertures per square inch therein with an average aperture size of 4/64 × 6/64 inches. After drying, a 3 inch × 1 yard bandage strip weighing 45 grams is subjected to the Green Strength Test procedure. The results are reported in Table II.

EXAMPLE 4

The slurry composition of Table I is coated on one side of a nonwoven 100% polyester fabric of 0.95 ounce weight per square yard having 96 apertures per square inch therein with an average aperture size of 4/64 × 4/64 inches. After drying, a 3 inch × 1 yard bandage strip weighing 39 grams is subjected to the Green Strength Test procedure. The results are reported in Table II.

EXAMPLE 5

The slurry composition of Table I is coated on one side of a nonwoven 100% polyester fabric of 0.95 ounce weight per square yard having 162 apertures per square inch therein, with an average aperture size of 3/64 × 2/64 inches. After drying, a 3 inch × 1 yard bandage strip weighing 35 grams is subjected to the Green Strength Test procedure. The results are reported in Table II.

EXAMPLE 6

The slurry composition of Table I is coated on one side of a nonwoven 100% polyester fabric of 0.7 ounce weight per square yard having 98 apertures per square inch therein with an average aperture size of 5/64 × 5/64 inches. After drying, a 3 inch × 1 yard bandage strip weighing 40 grams is subjected to the Green Strength Test procedure. The results are reported in Table II.

EXAMPLE 7

The slurry composition of Table I is coated on one side of a nonwoven 100% polyester fabric of 0.7 ounce weight per square yard having 162 apertures per square inch therein with an average aperture size of 3/64 × 3/64 inches. After drying, a 3 inch × 1 yard bandage strip weighing 37 grams is subjected to the Green Strength Test procedure. The results are reported in Table II.

EXAMPLE 8

The slurry composition of Table I is coated on one side of a 32 × 28 count gauze. After drying, four 3 inch by 1 yard bandage strips weighing 31.5, 36.0, 34.0 and 36.0 grams respectively are subjected to the Green Strength Test procedure. The results of the tests are reported in Table II.

EXAMPLE 9

The slurry composition of Table I is coated on one side of a nonwoven 50/50 polyester/rayon fabric bonded with an acrylic/vinyl acetate copolymer latex binder. The fabric has 0.83 ounce weight per square yard and 144 apertures per square inch therein. After drying a 3 inch by 1 yard bandage strip weighing 19.5 grams is subjected to the Green Strength Test procedure. The results are reported in Table II.

EXAMPLE 10

The slurry composition of Table I is coated on one side of a nonwoven 100% polyester fabric bonded with an acrylic/vinyl acetate copolymer latex binder. The fabric has 0.87 ounce weight per square yard and 95 apertures per square inch therein. After drying, a 3 inch by 1 yard bandage strip weighing 30 grams is subjected to the Green Strength Test procedure. The results are reported in Table II.

TABLE II

| Example | Fabric Weight (ounce/sq. yard) | Dry Bandage Weight (grams) | One Hour Green Strength (pounds) | % One Hour Green Strength Over Average Green Strength of 4 Reference Gauze Samples |
| --- | --- | --- | --- | --- |
| 1 | 1.00 | 41.0 | 155 | 1.22 |
| 2 | 0.90 | 40.0 | 220 | 1.73 |
| 3 | 1.10 | 45.0 | 180 | 1.41 |
| 4 | 0.95 | 39.0 | 200 | 1.57 |
| 5 | 0.95 | 35.0 | 190 | 1.49 |
| 6 | 0.70 | 40.0 | 220 | 1.73 |
| 7 | 0.70 | 37.0 | 180 | 1.41 |
| 8a | 32 × 28 count gauze | 31.5 | 135 ⎫ | |
| 8b | " | 36.0 | 130 ⎬ 127.5 | |
| 8c | " | 34.0 | 120 ⎭ Average | |
| 8d | " | 36.0 | 125 | |
| 9 | 0.83 | 19.5 | Too weak for measurment | |

TABLE II-continued

| Example | Fabric Weight (ounce/sq. yard) | Dry Bandage Weight (grams) | One Hour Green Strength (pounds) | % One Hour Green Strength Over Average Green Strength of 4 Reference Gauze Samples |
|---|---|---|---|---|
| 10 | 0.87 | 30.0 | 95 | 0.75 |

The results shown in Table II, demonstrate that substantially higher green strengths are exhibited by the embodiments (Examples 1 through 7) of the present invention than by conventional gauze bandages (Examples 8a through 8d) or by a bandage made of nonwoven fabric other than polyester (Example 9 or by a bandage made of a nonwoven 100% polyester fabric containing a binder therein (Example 10).

Examples 11 through 13 illustrate still other embodiments of the orthopedic bandages of the present invention, tested for green strength along with reference gauze samples of Examples 14a and 14b, and a rayon sample of Example 15. These samples were run under approximately identical experimental conditions.

EXAMPLE 11

The slurry composition of Table I is coated on both sides of a nonwoven 100% polyester fabric of 1.4 ounce weight per square yard having 283 apertures per square inch therein, with an average aperture size of 1/32 × 1/32 inches. After drying, a 3 inch × 1 yard bandage strip weighing 43 grams is subjected to the Green Strength Test procedure. The results are reported in Table III.

EXAMPLE 12

The slurry composition of Table I is coated on both sides of a nonwoven 100% polyester fabric of 1.0 ounce weight per square yard having 145 apertures per square inch therein, with an average aperture size of 3/64 × 2/32 inches. After drying, a 3 inch × 1 yard bandage strip weighing 48 grams is subjected to the Green Strength Test procedure. The results are reported in Table III.

EXAMPLE 13

The slurry composition of Table I is coated on both sides of a nonwoven 100% polyester fabric of 1.4 ounce weight per square yard having 256 apertures per square inch therein, with an average aperture size of 1/32 × 1/32 inches. After drying, a 3 inch × 1 yard bandage strip weighing 66 grams is subjected to the Green Strength Test procedure. The results are reported in Table III.

EXAMPLE 14

The slurry composition of Table I is coated on both sides of a 32 × 28 count gauze. After drying, two 3 inch by 1 yard bandage strips weighing 49 grams and 51 grams respectively are subjected to the Green Strength Test procedure. The results are reported in Table III.

EXAMPLE 15

The slurry composition of Table I is coated on both sides of a nonwoven rayon fabric of 1.2 ounce weight per square yard having 256 apertures per square inch therein, with an average aperture size of 1/32 × 1/32 inches. After drying, a 3 inch × 1 yard bandage strip weighing 56 grams is subjected to the Green Strength Test procedure. The results are reported in Table III.

TABLE III

| Example | Fabric Weight (ounce/sq. yard) | Dry Bandage Weight (grams) | One Hour Green Strength (pounds) | % One Hour Green Strength Over That of Reference Gauze Sample |
|---|---|---|---|---|
| 11 | 1.4 | 43.0 | 107 | 1.59 |
| 12 | 1.0 | 48.0 | 135 | 2.00 |
| 13 | 1.4 | 66.0 | 142 | 2.10 |
| 14a | 32 × 28 count gauze | 49.0 | 65 } 67.5 | |
| 14b | 32 × 28 count gauze | 51.0 | 70 } | |
| 15 | 1.2 | 56.0 | 50 | 0.74 |

The results shown in Table III demonstrate that substantially higher green strengths are exhibited by the embodiments (Examples 11 through 13) of the present invention than by conventional gauze bandages (Examples 14a and 14b) or by a bandage made of a nonwoven rayon fabric.

From the above description, it is apparent that the objects of the present invention have been acheived. While only certain embodiments have been illustrated specifically, many alternative modifications will be apparent from the above description to those skilled in the art. These and other alternatives are considered within the spirit and scope of the present invention and coverage thereof is intended by the claims that follow.

What is claimed is:

1. A highly conformable orthopedic bandage of improved green strength comprising: a textile-like, apertured, porous, nonwoven polyester fabric of essentially unbonded, mechanically entangled fibers randomly entangled with each other in a pattern of localized entangled regions interconnected by fibers extending between adjacent entangled regions and having a tensile strength of at least 1.0 pound per inch width of the fabric, an extent of elongation of from about 25 to about 100% in machine direction and of from about 40 to about 120% in cross direction of its relaxed length and width respectively, a fabric weight of from about 0.5 to about 3.0 ounces per square yard, a degree of openness defined by the presence of 50 to 500 apertures per square inch with an aperture size of from about 1/64 × 1/64 to about ⅛ × ⅛ inches; said fabric impregnated with a settable plaster of Paris composition.

2. The orthopedic bandage of claim 1 wherein said plaster of Paris composition is coated onto said nonwoven polyester fabric from a slurry composition comprising plaster of Paris, and about 30 to about 85 parts by weight of water per 100 parts by weight of said plaster of Paris.

3. The orthopedic bandage of claim 1 wherein said fabric has a tensile strength of at least about 3 pounds per inch width, an extent of elongation of about 35 to 90% in machine direction and of about 40 to 110% in cross direction of its relaxed length and width respectively, a degree of openness of about 80 to 200 apertures per square inch with an aperture size of about 3/64 × 3/64 to 7/64 × 7/64 inches.

* * * * *